United States Patent [19]

Maffia

[11] Patent Number: 4,533,780
[45] Date of Patent: Aug. 6, 1985

[54] NATURAL GAS CONVERSION

[75] Inventor: Gennaro J. Maffia, Wallingford, Pa.

[73] Assignee: Atlantic Richfield Company, Los Angeles, Calif.

[21] Appl. No.: 601,139

[22] Filed: Apr. 16, 1984

[51] Int. Cl.$^3$ ............................................... C07C 1/00
[52] U.S. Cl. .................................... 585/330; 585/500; 585/656
[58] Field of Search ..................... 585/330, 500, 656

[56] References Cited

U.S. PATENT DOCUMENTS 4,293,722 10/1981 Ward et al. ........................ 585/330
4,443,644 4/1984 Jones et al. ........................ 585/500

Primary Examiner—Curtis R. Davis
Attorney, Agent, or Firm—Craig E. Larson

[57] ABSTRACT

A method of synthesizing hydrocarbons from a methane source which includes the steps of separating a mixture of lower alkanes to form a first fraction containing predominately methane and at least one second fraction containing predominately $C_2+$ alkanes; dehydrogenating the second $C_2+$ fraction to form an effluent comprising $C_2+$ olefins; contacting the methane fraction with an oxide of a metal which oxide when contacted with methane at between about 500° and 1000° C. is reduced and produces higher hydrocarbon products and water; and oligomerizing the $C_2+$ olefin fraction and the methane contacting effluent to produce higher hydrocarbon products.

2 Claims, No Drawings

NATURAL GAS CONVERSION

BACKGROUND OF THE INVENTION

This invention relates to the conversion of hydrocarbons to higher hydrocarbons. This invention more particularly relates to the conversion of normally gaseous alkanes into normally liquid hydrocarbons. This invention is especially concerned with the conversion of natural gas to higher hydrocarbons, preferably normally liquid hydrocarbons.

The composition of natural gas at the wellhead varies. For example, the methane content of natural gas may vary from about 40 to about 95 vol. %. Other constituents of natural gas include ethane, propane, butanes, pentanes (and heavier hydrocarbons), hydrogen sulfide, carbon dioxide, helium and nitrogen.

Natural gases are classified as dry or wet depending on the amount of condensable hydrocarbons contained in it. Condensable hydrocarbons generally comprise $C_3+$ alkanes although some ethane may also be included. Gas conditioning is conventionally employed to alter the composition of wellhead gas, processing facilities usually being located in or near production fields. Conventional processing of wellhead natural gas yields processed natural gas containing at least a major amount of methane that also yield natural gas liquids containing, predominantly, $C_3+$ alkanes.

Considerable attention has been devoted to finding economic means for producing synthetic fuels from natural gas or other feedstock composed of lower alkanes. One approach which has been extensively studied comprises natural gas to synthesis gas (mixtures comprising CO and $H_2$) which is then either converted directly to higher hydrocarbons (broadly referred to as a "Fischer-Tropsch" conversion) or first converted to methanol which is subsequently converted to higher hydrocarbons (e.g., by use of the Mobil methanol-to-gasoline processes). A substantial difficulty with both of these synthesis gas-based methods is the formation of oxygenates, which complicates further processing of liquid products using conventional petroleum refining techniques. As demonstrated by the Sasol plants in South Africa such further processing requires customized refining techniques, particularly adapted to the unique feedstock produced. A process capable of converting methane and/or lower alkanes to hydrocarbons compatible with conventional refinery feedstock would therefore be of substantial value to the industry.

Large-scale use of natural gas often requires a sophisticated and extensive pipeline system. Liquefacation has also been employed as a transportation means, but processes for liquifying, transporting and revaporizing natural gas are complex and energy-intensive and require extensive safety precautions. Transport of natural gas has been a continuing problem in the exploitation of natural gas resources. It would be extremely valuable to be able to convert natural gas to more readily handable or transportable products. Moreover, improved methods for the conversion of natural gas would be of value to the chemical industry.

One object of this invention is a method for converting natural gas, especially wet natural gas, to higher hydrocarbons, especially normally liquid hydrocarbons. A related object is a method for converting lower alkanes to higher hydrocarbon products which are compatible with conventional petroleum refinery feedstocks for the purpose of further processing to more valuable hydrocarbon products. A further object of this invention is a method for converting natural gas to more easily transportable products. A still further object of this invention is an improved method for converting natural gas to higher hydrocarbon products wherein the yield of normally liquid hydrocarbohs is enhanced.

Other aspects, objects and the several advantages of the invention will become to those skilled in the art upon reading this disclosure and the appended claims.

SUMMARY OF THE INVENTION

A method for converting lower alkanes to higher hydrocarbon products has now been discovered which method comprises:

(a) separating a mixture comprising lower alkanes to form a first fraction containing predominately methane and at least one second fraction containing predominately $C_2+$ alkanes;

(b) dehydrogenating said second fraction(s) to form a dehydrogenation effluent comprising $C_2+$ olefins;

(c) contacting said first fraction with a solid to form a redox effluent comprising $C_2+$. olefins, said solid comprising at least one reducible oxide of at least one metal which oxide(s) when contacted with methane at temperatures selected within the range of about 500° to 1000° C. are reduced and produce higher hydrocarbon products; and (d) oligomerizing the $C_2+$ olefins of said dehydrogenation effluent and said redox effluent to form higher hydrocarbon products.

DETAILED DESCRIPTION OF THE INVENTION

Broadly, any feedstock comprising lower alkanes may be employed in the process of this invention. Preferred feedstocks are derived from natural gas, but this invention is not limited thereto. A more particularly preferred feedstock is wet natural gas. The feedstock may contain other organic or inorganic constituents. Typically the lower alkanes will consist of hydrocarbons containing from 1 to 5 carbon atoms per molecule.

The first step of the method of this invention comprises separating the mixtures comprising lower alkanes to form a first fraction containing predominately methane and at least one second fraction containing predominately $C_2+$ alkanes. Various methods and means for effecting the separation are well-known in the art. For example, the various techniques for separating condensable hydrocarbons from natural gas may be employed. Most such techniques effect a rough separation of natural gas to form: (1) a gas fraction which is predominately methane but also contains significant amounts of ethane and (2) a natural gas liquids fraction (composed of $C_3+$ alkanes with varying amounts of ethane). Also included within the scope of the separation of this invention are methods which effect a more complete separation of methane from higher alkanes. Such more complete separation techniques are currently preferred for use in process of this invention.

Also included in aspects of the present invention particularly concerned with producing more readily transportable material from natural gas is the removal of higher alkanes (e.g., in the $C_5+$ range) from the $C_2+$ fraction prior to the subsequent dehydrogenation step. Such separations are included within the broader scope of this invention.

The second step of the method of this invention comprises dehydrogenating the fraction(s) containing predominately $C_{2+}$ alkanes, separated in the first step, to produce $C_{2+}$ olefins. It will be apparent to one skilled in the art that separate dehydrogenation of different $C_{2+}$ alkane cuts may sometimes be desirable. However, in a currently preferred embodiment of the process of this invention, a single $C_{2+}$ alkane fraction is separated in the first step and dehydrogenated to form $C_{2+}$ olefins.

The dehydrogenation technique employed is not narrowly critical to this invention. Thus, such techniques as thermal dehydrogenation (i.e., pyrolysis or steam cracking), catalytic dehydrogenation (e.g., dehydrogenation over catalysts such as chromia-alumina, calcium nickel phosphate stabilized chromium oxide, etc.), and oxidative dehydrogenation (e.g., dehydrogenation over solids such as bismuthmolybdate, Mg-Cr-ferrites, Mn-ferrites, and other metal oxides and salts to produce dehydrogenated products and coproduct water) may be employed.

The presently preferred method of dehydrogenation is oxidative dehydrogenation. Presently preferred oxidative dehydrogenation solids (or catalysts) include those solids, described below, which may be employed for the conversion of methane to higher hydrocarbons. See also concurrently filed U.S. patent application Ser. Nos. 06/600,655; 06/600,916; 06/600,735; 06/600,652; 06/600,915; 06/600,734; 06/600,736; and 06/600,651, the entire contents of which are incorporated herein by reference.

The third step of the method of this invention comprises contacting the fraction containing predominately methane, separated in the first step, with a contact solid to form a redox effluent comprising $C_{2+}$ olefins.

The solid which is contacted with methane in the third step of the present process has heretofore been generally referred to as an oxidative synthesizing agent. Oxidative synthesizing agents comprise at least one oxide of at least one metal, which oxides when contacted with methane at temperatures selected within the range of about 500° to 1000° C. produce higher hydrocarbon products, coproduct water and a reduced metal oxide. The composition thus contains at least one reducible oxide of at least one metal. The term "reducible" identifies those oxides of metals which are reduced by the methane contact. The term "oxide(s) of metal(s)" includes: (1) one or more metal oxides (i.e., compounds described by the general formula $M_xO_y$ herein M and of the subscripts x and y designate the relative atomic proportions of metal and oxide in the composition) and/or (2) one or more oxygen-containing metal compounds, provided that such oxides and compounds have the capability of performing to produce higher hydrocarbon products as set forth herein.

Effective solids for the conversion of methane to higher hydrocarbons have previously been found to comprise reducible oxides of metals selected from the group consisting fo manganese, tin, indium, germanium, antimony, lead, bismuth and mixtures thereof. See commonly-assigned U.S. patent application Ser. No. 522,925; now U.S. Pat. No. 4,443,649; Ser. No. 522,944, now U.S. Pat. No. 4,444,984; Ser. No. 522,942, now U.S. Pat. No. 4,443,648; Ser. No. 522,905, now U.S. Pat. No. 4,443,645; Ser. No. 522,887, now U.S. Pat. No. 4,443,647; Ser. No. 522,876, now U.S. Pat. No. 4,443,644; and Ser. No. 522,906, now U.S. Pat. No. 4,443,646 all filed Aug. 12, 1983, the entire contents are incorporated herein by reference. Alkali and alkaline earth metals and compounds thereof have been found to improve the hydrocarbon product selectivity of these solids. The further incorporation of phosphorus into solids promoted by alkali or alkaline earth components enhances catalyst stability. See commonly-assigned U.S. patent application Ser. Nos. 522,937 and 522,936, both filed Aug. 12, 1983, the entire contents of which are incorporated herein by reference.

Reducible oxides of cerium, praseodymium, and terbium have also been found to be effective for the conversion of methane to higher hydrocarbons when the rare earth component is associated with an alkali or alkaline earth metal component. See concurrently filed U.S. patent application Ser. Nos. 06/600,665; 06/600,918; and 06/600,917, the entire contents of which are incorporated herein by reference.

Commonly-assigned U.S. patent application Ser. No. 06/600,730 discloses and claims a process for the conversion of methane to higher hydrocarbons which comprises contacting methane with a contact solid comprising a reducible oxide of iron and at least one member of the group consisting of alkali metals, alkaline earth metals, and compounds thereof. This application is incorporated herein by reference.

Commonly-assigned U.S. patent application Ser. No. 06/600,969 discloses and claims a process for the conversion of methane to higher hydrocarbons which comprises contacting methane with a contact solid comprising a reducible oxide of ruthenium and at least one member of the group consisting of alkali metals, alkaline earth metals, and compounds thereof. This application is incorporated herein by reference.

The metal components may be associated with other support materials such as silica, magnesia, alumina, titania, zirconia and the like and combinations thereof. When employing solids containing rare earth components—oxides of Ce, Pr and Tb—the rare earth oxides preferably serve as supports.

Reducible oxides of manganese have been found to be particularly desirable for methane conversion, especially when associated with an alkali metal component (preferably sodium). Especially preferred solids comprise silica- and/or magnesia-supported solids containing oxides of manganese and sodium.

The solids contacted with methane in the third step of the present invention can be prepared by any suitable method. Conventional methods such as precipitation, coprecipitation, impregnation or dry mixing can be used. Supported solids may be prepared by methods such as adsorption, impregnation, precipitation, coprecipitation, and dry mixing. When phosphorus is incorporated into the solid, it is desirable to provide it in the form of a phosphate of an alkali or alkaline earth metal.

A suitable method of preparation is to impregnate a support with solutions of the desired metals. Suitable compounds for impregnation include the acetates, acetylacetonates, oxides, carbides, carbonates, hydroxides, sulfides, tartrates, fluorides, chlorides, bromides, or iodies. After impregnation the preparation is dried to remove solvent and the dried solids calcined, preferably in air, at a temperature within the range of about 300° to 1200° C. Particular calcination temperatures will vary depending upon the particular metal compound or compounds employed.

Regardless of how the components of the solids are combined, the composite will be dried and calcined at elevated temperatures prior to use in the process of this invention.

Preferably, methane is contacted with the solid in the substantial absence of catalytically effective nickel, noble metals and compounds thereof (i.e., nickel, rhodium, palladium, silver, osmium, irridium, platinum, and gold) to minimize the deleterious catalytic effects thereof. These metals, when contacted with methane at the temperatures employed in the third step of the present invention, tend to promote coke formation, and the metal oxides tend to promote the formation of combustion products rather than the desired hydrocarbons. The term "catalytically effective" is used herein to identify that quantity of one or more nickel and the noble metals and compounds thereof which substantially changes the distribution of products obtained in the third step of this invention relative to such contacting in the absence of such metals and compounds thereof.

Operating temperatures for the third step of the method of the invention are generally within the range of about 500° to 1000° C. If reducible oxides of metals such as In, Ge or Bi are present in the solid, the particular temperature selected may depend, in part, on the particular reducible metal oxide(s) employed. Thus, reducible oxides of certain metals may require operating temperatures below the upper part of the recited range to minimize sublimation or volatilization of the metals (or compounds) during methane contact. Examples are: reducible oxides of indium, (operating temperatures will preferably not exceed about 850° C.) (2) reducible oxides of germanium (operating temperatures will not exceed about 850° C.) and (3) reducible oxides of bismuth (operating temperatures will not exceed about 850° C.).

Operating pressures for the methane contacting step are not critical to the presently claimed invention. However, general system pressure and partial pressure of methane have been found to effect overall results. Preferred operating pressures are within the range of about 1 to 30 atmospheres. See commonly-assigned U.S. patent application Ser. No. 522,935, filed Aug. 12, 1983, the entire content of which are incorporated herein, which discloses a process which comprises contacting methane with an oxidative synthesizing agent under elevated pressure to produce greater amounts of $C_3+$ hydrocarbon products.

Contacting methane and a reducible metal oxide to form higher hydrocarbons from methane also produces a reduced metal oxide and coproduct water. The exact nature of the reduced oxides are unknown, and so are referred to herein as "reduced metal oxides". Regeneration of a reducible metal oxide is readily accomplished by contacting such reduced materials with oxygen (e.g., an oxygen-containing gas such as air) at elevated temperatures, preferably at a temperature selected within the range of about 300° to 1200° C., the particular temperature selected depended upon the metal(s) included in the solid.

In carrying out the third step of the present process, a single reactor apparatus containing fixed beds of solids may be used with intermittent or pulsed flow of a first gas comprising methane and second gas comprising oxygen (e.g., oxygen- oxygen diluted with an inert gas or air, preferably air). See concurrently filed U.S. patent application Ser. No. 06/601,143, the entire content of which is incorporated herein by reference. The methane contacting step and the oxygen contacting step may also be performed in physically separate zones with solids recirculating between the two zones. See commonly-assigned U.S. patent application Ser. No. 522,938, filed Aug. 12, 1983, the entire content of which is incorporated herein by reference.

Thus, one suitable method for synthesizing hydrocarbons from a methane source comprising: (a) contacting a gas comprising methane and particles comprising at least one reducible oxide of at least one metal to form higher hydrocarbon products, coproduct water, and reduced metal oxide; (b) removing particles comprising metal oxide from the first zone and contacting the reduced particles in a second zone with a oxygen-containing gas to form particles comprising a reducible metal oxide; and (c) returning the particles produced in the second zone to the first zone. The steps are preferably repeated at least periodically, and more preferably the steps are continuous. In one more preferred embodiment solids are continuously circulated between at least one methane contact zone and at least one oxygen contact zone.

Particles comprising a reducible metal oxide which are contacted with methane may be maintained as fluidized, ebullating, or entrained beds of solids. Preferably methane is contacted with a fluidized bed of solids.

Similarly, particles comprising reduced metal oxide which are contacted with oxygen may be maintained as fluidized, ebullating or entrained beds of solids. Preferably oxygen is contacted with a fluidized bed of solids.

In one more preferred embodiment of the present invention methane feedstock and particles comprising promoted oxidative synthesizing agent are continuously introduced into a methane contact zone maintained at synthesizing conditions. Synthesizing conditions include the temperatures and pressures described above. Gaseous reaction products from the methane contact zone (separated from entrained solid) may be further processed—e.g., they may be passed through a fractioning system wherein the desired hydrocarbon products are separated from unconverted methane and combustion products. Unconverted methane may be recovered and recycled to the methane contact zone.

Particles comprising reduced metal oxide are contacted with oxygen in an oxygen contact zone for a time sufficient to oxidize at least a portion of the reduced oxide to produce a reducible metal oxide and to remove, i.e., combust, at least a portion of any carbonaceous deposit which may form on the particles in the methane contact zone. The conditions of the oxygen contact zone will preferably include a temperature selected within the range of about 300° to 1200° C., pressures of up to about 30 atmospheres, and average particle contact time within the range of about 1 to 120 minutes. Sufficient oxygen is preferably provided to oxidize all reduced metal oxide to produce a reducible oxide and to completely combust any carbonaceous material deposited on the particles. At least a portion of the particles comprising promoted oxidative synthesizing agent which are produced in the oxygen contact zone are returned to the methane contact zone.

The rate of solids withdrawal from the methane contact zone is desirably balanced with the rate of solids passing from the oxygen contact zone to the methane contact zone so as to maintain a substantially constant inventory of particles in the methane contact zone, thereby enabling steady state operation of the synthesizing system.

The effluent produced by the third step of the method of this invention comprises unconverted methane and higher hydrocarbons (especially methane and ethylene), as well as carbon oxides and water. The effluent is referred to herein as "redox effluent". It is within the scope of the present invention to recover a portion of the redox effluent (e.g., methane) for recycle to the methane contact zone. Similarly, carbon oxides and water may be removed from the redox effluent prior to further treatment of the effluent in accordance with the present invention.

Whether or not such intermediate separations are employed, a gas stream comprising $C_{2+}$ olefins is recovered from the redox effluent and is passed to the fourth step of the process of this invention wherein olefins are oligomerized to produce higher hydrocarbon products.

The fourth step of the method of this invention comprises oligomerizing the $C_{2+}$ olefins present in the dehydrogenation effluent and in the redox effluent to form higher hydrocarbon products. The oligomerization techniques employed are not narrowly critical to this invention. See, for example, concurrently filed U.S. patent application Ser. No. 06/600,657, the entire contents of which are incorporated herein by reference. The combined effluents from the dehydrogenation and methane steps of this invention will typically comprise a mixture of olefins containing a major amount of diluent. Techniques for oligomerizing such a mixture are disclosed in concurrently filed U.S. patent application Ser. Nos. 06/604,785 and 06/601,144, the entire contents of which are incorporated herein by reference.

It is also within the scope of the present invention to oligomerize the $C_{2+}$ olefins contained in the dehydrogenation and redox effluents separately. However, one principle advantage of a preferred embodiment of this invention is the enhanced efficiencies realized when the effluents are combined and oligomerized.

Also within the scope of the present invention are flow schemes wherein the effluents are combined and then fractionated to recover various cuts of $C_{2+}$ olefins. Such will be apparent to one skilled in the art. Again, however, in a one embodiment of this invention, it is not necessary to perform such a fractionation.

In addition to olefins, the redox effluent may contain varying amounts of $C_{2+}$ alkanes. Moreover, some alkane formation may occur while oligomerizing $C_{2+}$ olefins. Concurrently filed U.S. patent application Ser. No. 06/600,878, the entire content of which is incorporated herein by reference, discloses the separation and recycle of $C_{2+}$ alkanes from process streams derived from the redox effluent to a methane conversion zone. Separation of $C_{2+}$ alkanes from the process streams may occur at various points in a process comprising methane conversion to olefins and olefin oligomerization to higher hydrocarbons. Such separation and recycle is within the scope of the present invention.

However, in a preferred, distinct, embodiment of the present invention, $C_{2+}$ alkanes recovered from the redox effluent and/or $C_{2+}$ alkanes recovered from process streams derived from the redox or dehydrogenation effluents during the oligomerization step of the present invention are recycled to the second, dehydrogenation step of this invention. Such recycle enchances the overall hydrocarbon conversion efficiencies attained by the more general method of this invention.

What is claimed is:

1. A method for converting lower alkanes to higher hydrocarbon products which comprises:
    (a) separating a mixture comprising lower alkanes to form a first fraction enriched in methane relative to said mixture and at least one second fraction enriched in $C_{2+}$ alkanes relative to said mixture;
    (b) dehydrogenating said second fraction to form a dehydrogenation effluent comprising $C_{2+}$ olefins;
    (c) contacting said first fraction with a solid to form a redox effluent comprising $C_{2+}$ olefins, said solid comprising at least one reducible oxide of at least one metal which oxides when contacted with methane at temperatures selected within the range of about 500° to 1000° C. are reduced and produce higher hydrocarbon products and water; and
    (d) oligomerizing the $C_{2+}$ olefins in said dehydrogenation effluent and in said redox effluent to form higher hydrocarbon products.

2. The method of claim 1 wherein at least one fraction comprising $C_{2+}$ alkanes is separated from said redox effluent or from process streams derived from said dehydrogenation and redox effluents and said fraction(s) is dehydrogenated as recited in step (b).

* * * * *